United States Patent [19]

McGregor et al.

[11] 4,082,737

[45] Apr. 4, 1978

[54] STABILIZED THYMOSIN COMPOSITION AND METHOD

[75] Inventors: Weldon Courtney McGregor, Montville; Harold Leon Newmark, Maplewood; Armin Hermann Ramel, Mountain Lakes, all of N.J.

[73] Assignee: Hoffmann-La Roche Inc., Nutley, N.J.

[21] Appl. No.: 770,480

[22] Filed: Feb. 22, 1977

[51] Int. Cl.² ..................... C07C 103/52; A61K 37/00
[52] U.S. Cl. ............................. 260/112.5 R; 424/177
[58] Field of Search .................. 260/112.5 R; 424/177

[56] References Cited

U.S. PATENT DOCUMENTS

| | | | |
|---|---|---|---|
| 4,002,602 | 1/1977 | Goldstein | 260/112.5 R |
| 4,002,740 | 1/1977 | Goldstein et al. | 260/112.5 R |
| 4,010,148 | 3/1977 | Goldstein | 260/112.5 R |

OTHER PUBLICATIONS

Ohkido, Chem. Abst., 79, 1973, p. 129041z.
Shimizu, et al., Chem. Abst., 80, 1974, p. 112675g.

*Primary Examiner*—Delbert R. Phillips
*Attorney, Agent, or Firm*—Samuel L. Welt; Jon S. Saxe

[57] ABSTRACT

Thymosin fraction 5 has been widely employed recently in the clinical investigation of this thymic hormone. This material is a hormonally active proteinaceous composition which is involved in the regulation of cell-mediated immunity. The present disclosure provides a solid, stable, endotoxin and pyrogen free thymosin fraction 5 composition suitable for reconstitution for injection.

7 Claims, No Drawings

STABILIZED THYMOSIN COMPOSITION AND METHOD

BACKGROUND OF THE INVENTION

A process for preparing thymosin fraction 5 is disclosed in U.S. patent application Ser. No. 576,509, filed May 12, 1975, now U.S. Pat. No. 4,010,148. In spite of the fact that such process utilizes an ultrafiltration step, because of subsequent steps, the resulting product is not completely endotoxin and pyrogen free.

The use of ultrafiltration to effect removal of pyrogens from injectable drug preparations has been reported. See for example Chemical Abstracts, Vol. 79, Issue 22, Section 61, Abstract No. 129041; Chemical Abstracts, Vol. 80, Issue 20, Section 63, Abstract No. 112675 (based on Japanese Pat. No. 73 35445); and Chemical Abstracts, Vol. 83, Issue 20, Section 63, Abstract No. 168487 (based on Japanese Pat. No. 75100220).

Additionally, Rubio and Lopez, Appl. Microbiol. 23, 211 (1972) have disclosed the purification of endotoxins from *Pseudomonas aeruginosa* using a membrane with molecular weight cut off of 100,000. The concentration of endotoxin in the permeate was, however, not reported.

DESCRIPTION OF THE INVENTION

It is generally believed that most pyrogens are bacterial endotoxins which are characterized as complexes of protein, phospholipid and lipopolysaccharide having a molecular weight in the range of 1-20 million. Although the lipopolysaccharide (LPS) moiety of *Salmonella sp* endotoxin, for example, has been shown to have a molecular weight of approximately 3350, LPS generally has a marked tendency to aggregate, so that under normal laboratory conditions the apparent molecular weight of endotoxins and/or LPS is substantially higher.

It has now been found, and as such represents an aspect of the present invention, that endotoxins and pyrogens can be virtually completely removed from solutions of purified thymosin fraction 5 by carrying out an ultrafiltration as the final step. The ultrafiltration utilizes a membrane with a manufacturer rated cut off of 10,000 molecular weight and the thymosin fraction 5 components pass through the membrane while the endotoxins and pyrogens are retained.

It has been repeatedly demonstrated that thymosin fraction 5 components were aggregated following a column desalting step. The aggregates failed to pass through the 10,000 MW cut-off membrane even though the sample had permeated the same membrane in a previous processing step. The aggregates could be broken up by increasing the ionic strength with various salts at pH 7 or above. Ammonium bicarbonate was chosen for the process because it provided a pH of 8.0 at which the fraction 5 was readily soluble and the salt evaporated during lyophilization. A concentration of 0.1M-0.5M (salt added directly to the column eluate) was routinely used. At low ionic strength (with no salt added) the loss of protein during ultrafiltration was $\leq$ 50% and the activity loss was 100%.

Additionally, it has been found that in order to achieve complete, consistent and reproducible removal of endotoxins and pyrogens it was necessary that the ultrafiltration equipment be thoroughly cleaned and detoxified before each run. Thus, for example, prior to each run the cartridges were washed with 1-2M NaCl solution followed by distilled water and then stored in sodium hypochorite solution (100 ppm). Immediately prior to use the cartidges were soaked overnight, both shell and tube side, and ancillary lines in dilute caustic (1% NaOH) solution.

While the aforesaid procedure provides a sterile endotoxin and pyrogen free solution of thymosin fraction 5, it does not provide a convenient form to store and ship this material for clinical use. Thus it has heretofore been necessary to aseptically subdivide this material into sterile vials and ship in a frozen condition over dry ice. Storage until use also required maintenance in a frozen condition. It should be noted that thymosin fraction 5 contains a very high percentage of polypeptides which are excellent nutrients for microbial growth. Thus any thawing during shipment or storage could allow growth of accidently introduced microorganisms. When ready for use, the vials must be thawed from the frozen state, a rather time consuming and inconvenient situation.

It has now further been found that thymosin fraction 5, after the removal of the endotoxins and pyrogens by ultrafiltration, can be converted to a solid, stable, endotoxin and pyrogen free form. Such form is readily achieved by freeze-drying (lyophilization) of the sterile solution in aseptically subdivided sterile vials. It has unexpectedly been discovered that addition of a phenolic type antimicrobial agent to the thymosin fraction 5 solution prior to lyophilization will result in incorportion of the entire amount of the antimicrobial agent into the solid product even though such agents are volatile and would be expected to be removed with the solvent. Suitable phenolic type antimicrobials useful in the practice of this aspect of the present invention include phenol, cresols, and the pharmaceutically acceptable esters of para hydroxy benzoic acid, such as propyl and methyl. Phenol is a particularly preferred antimicrobial. The final solid, stable composition will contain from 0.5 to 25%, most preferably 5 to 20% antimicrobial agent.

Thymosin fraction 5 comprises a mixture of polypeptides with an isoelectric point below pH 6 which are properly solubilized at a pH well above the iso-electric for optimum solubilization with a minimum risk of irritation to the tissues at injection. In order to effectuate proper pH at reconstitution, the composition of the present invention is provided with a buffer. A preferred buffer for this purpose is sodium bicarbonate, said buffer being added in sufficient amount to provide a solution pH of 7 to 8.

In a preferred embodiment 30 to 40 liters of desalted aqueous column eluate containing 1-2 mg/ml of thymosin fraction 5 peptides were ultrafiltered in a detoxified hollow fiber ultrafiltration unit (Amicon DC-30) containing three PM-10 cartridges, manufacturers rated molecular weight cut off of 10,000. The starting solution was buffered with a volatile, weakly basic buffer such as ammonium acetate or preferably ammonium bicarbonate (0.1-0.5M) which provided not only buffering, but the required ionic strength for ultrafiltration. The sample before ultrafiltration when assayed for endotoxins had concentrations greater than 1 ng/ml whereas the ultrafiltration permeate after lyophilization contained no detectable endotoxin, even a protein concentrations of 20 mg/ml, by the Limulus lysate assay. Moreover, the permeate exhibited an acceptable pyrogen level as measured by the rabbit fever test.

A total of 4.5 mg of phenol was added per 20 mg of thymosin fraction 5 in the permeate and the sterile, buffered permeate solution was subdivided into sterile vials and the vials freeze-dried, the final end conditions of the product in the lyophilizer being a temperature of 20°–30° C. at a vacuum of 10–20 microns of Hg.

We claim:

1. A solid stable endotoxin and pyrogen free form of thymosin fraction 5 comprising in combination:
    A. A major amount of thymosin fraction 5; and minor, effective amounts each of
    B. a phenolic type antimicrobial agent, selected from the group consisting phenol cresols and the pharmaceutically acceptable esters of para hydroxy benzoic acids and
    C. a buffering agent in an amount sufficient to provide a pH of 7–8 on reconstitution.

2. The composition of claim 1 wherein said antimicrobial agent is phenol.

3. The composition of claim 1 wherein the buffer agent is sodium bicarbonate.

4. A method for preparing a solid, stable endotoxin and pyrogen free form of thymosin fraction 5 which method comprises in combination:
    A. ultrafiltering an aqueous solution of thymosin fraction 5 buffered with a volatile weakly basic buffer to a pH of 7 to 8 through a membrane having a cut off of about molecular weight 10,000 whereby any endotoxins or pyrogen in said solution is retained in the concentrate and the thymosin fraction 5 is passed into the permeate;
    B. adding a phenolic type antimicrobial agent selected from the group consisting phenol cresols and the pharmaceutically acceptable esters of para hydroxy benzoic acids to said permeate; and
    C. lyophilizing said permeate, said phenolic type antimicrobial agent being retained with the lyophilized thymosin fraction 5.

5. The method of claim 4 wherein said aqueous solution of thymosin fraction 5 is buffered with ammonium bicarbonate.

6. The method of claim 5 wherein ammonium bicarbonate of a concentration in the range of about 0.1–0.5M is used.

7. The method of claim 4 wherein said phenolic type antimicrobial agent is phenol.

* * * * *